United States Patent [19]

Sofia

[11] Patent Number: 5,256,690

[45] Date of Patent: Oct. 26, 1993

[54] METHOD FOR TREATING AND CONTROLLING THE SYMPTOMS OF NEURODEGENERATIVE DISEASE AND NEUROPSYCHOPHARMACOLOGICAL DISORDERS

[75] Inventor: Robert D. Sofia, Willingboro, N.J.

[73] Assignee: Carter-Wallace, Inc., New York, N.Y.

[21] Appl. No.: 966,965

[22] Filed: Oct. 26, 1992

Related U.S. Application Data

[63] Continuation-in-part of Ser. No. 518,892, May 4, 1990, Pat. No. 5,055,489, and a continuation-in-part of Ser. No. 753,748, Sep. 3, 1991, abandoned.

[51] Int. Cl.⁵ ............................................. A61U 31/27
[52] U.S. Cl. .................................................... 514/483
[58] Field of Search ........................................ 514/483

[56] References Cited

U.S. PATENT DOCUMENTS 5,055,489 10/1991 Sofia .................................. 514/483
5,082,861 1/1992 Sofia .................................. 514/534

*Primary Examiner*—S. J. Friedman
*Attorney, Agent, or Firm*—Kevin B. Clarke

[57] ABSTRACT

A method for treating and controlling the symptoms of neuropsychopharmacological disorders and neurodegenerative diseases associated with or resulting from excessive activation of the N-methyl-D-aspartate receptor complex which comprises administering to warm-blooded animals in need of such treatment, 2-phenyl-1,3-propanediol dicarbamate, the neuroprotective effects of which are at least partially mediated through a strychnine-insensitive glycine receptor mechanism is disclosed.

4 Claims, No Drawings

METHOD FOR TREATING AND CONTROLLING THE SYMPTOMS OF NEURODEGENERATIVE DISEASE AND NEUROPSYCHOPHARMACOLOGICAL DISORDERS

This is a continuation-in-part of copending application(s) Ser. No. 07/518,892 filed May 4, 1990, now U.S. Pat. No. 5,055,489. Ser. No. 07/753,748 filed on Sep. 3, 1991, now abandoned.

This application is a Continuation-In-Part of pending U.S. patent application Ser. No. 07/518,892 filed May 4, 1990, now U.S. Pat. No. 5,055,489, and pending U.S. patent application Ser. No. 07/753,748 filed Sep. 3, 1991.

The present invention relates to pharmaceutical compositions containing 2-phenyl-1,3-propanediol dicarbamate (felbamate) as an active component and to methods for the treatment and control of the symptoms of neuropsychopharmacological disorders through the use of such compositions.

More particularly, the present invention relates to methods for treating and controlling the symptoms of neuropsychopharmacological disorders and neurodegenerative diseases associated with or resulting from excessive activation of the N-methyl-D-aspartate receptor complex.

BACKGROUND OF THE INVENTION

Neurochemical and electrophysiological studies have demonstrated that glycine modulates excitatory neurotransmission in the central nervous system. These actions are mediated through strychnine-insensitive glycine receptors with markedly different structural requirements for ligand binding and regional distribution than strychnine-sensitive sites associated with the role of glycine as an inhibitory neurotransmitter.

Neurotransmissions mediated through the N-methyl-D-aspartate (NMDA) receptor supramolecular complex are believed to be associated with numerous pathologic and physiologic mechanisms which include: kindling development, ischemic neuronal injury, synaptogenesis, spatial learning and long-term potentiation. Regulation of these neuronal mechanisms by NMDA-mediated processes is believed to involve activation of a receptor-gated ion channel.

Evidence now available clearly indicates that the NMDA complex is regulated, at least in part, by the amino acid glycine. Glycine has been shown to increase NMDA evoked currents in various tissues by increasing the opening frequency of the NMDA channel. Thus, NMDA-induced influx and intracellular accumulation of calcium are stimulated by glycine, which interacts with its own distinct site on the receptor. It is believed that the accumulation of intracellular calcium is implicated in the various neuropathologies.

Up to the present time, all drugs, including felbamate, used in the treatment of neuropsychopharmacological disorders and neurodegenerative diseases function as prophylactics against the symptoms of these disorders and diseases as opposed to being curatives.

In accordance with the present invention, it has been established that felbamate interacts with strychnine-insensitive glycine receptors and that felbamate's neuroprotective effects are at least in part mediated through a strychnine-insensitive glycine receptor mechanism.

Felbamate is a well known pharmaceutical compound having been described together with methods for its manufacture and use in U.S. Pat. Nos. 2,884,444; 4,868,327; 4,978,680; 5,055,489; 5,072,056 and 5,082,861.

One of the objects of the present invention is to provide methods and compositions for the treatment and control of the symptoms of neuropsychopharmacological disorders and neurodegenerative diseases.

Another object of the present invention to provide methods and compositions for the treatment and control of the symptoms of neuropsychopharmacological disorders and neurodegenerative diseases resulting from excessive activation of the NMDA through the use of felbamate.

Accordingly, it has been found that felbamate chemically described as 2-phenyl-1,3-propanediol dicarbamate is a compound which has demonstrated superior properties with respect to the treatment of disorders such as hypoxia, either alone, e.g. CO poisoning, near drowning; or combined with ischemic blood flow reduction, e.g. cardiac arrest, stroke; anxiety and neurodegenerative diseases, e.g. Guam ALS, Parkinson's disease, alzheimer's disease, dementia and lathyrism.

THE INVENTION

In the following examples, the ability of felbamate to interact with strychnine-insensitive glycine receptors is demonstrated. More particularly, in Example I, the radio ligand binding to glycine receptors is demonstrated using the antagonist [$^3$H]5,7-dichlorokynurenic acid, commonly referred to as [$^3$H]5,7DCKA which has been reported to bind with high affinity to glycine receptors in rat membranes. This radiolabeled compound is particularly suitable for purposes of demonstrating the present invention because of its high affinity and reliability within and between experiments.

In Example II, the neuroprotective effects of felbamate against hypoxic damage are demonstrated in the hippocampal slice model. This in vitro model simulates in vivo hypoxic-ischemic neuronal insults such as occur in stroke and other cerebral ischemic events.

EXAMPLE I

Male Sprague-Dawley rats weighing 150–200 g are housed under a 12-hour light/dark cycle with access to food and water ad libitum. Animals are anesthetized with $CO_2$ and sacrificed by decapitation. Brains are immediately removed and forebrains dissected, weighed and placed in 10 volumes (original wet weight volume) of 5 mM Hepes/4.5 mM Tris buffer (HTS; pH 7.8) containing 0.32 M sucrose. Tissue preparation is performed at about 4° C unless otherwise stated. Tissues are homogenized using a Brinkmann Polytron (setting 6, 30 seconds), diluted to 50 volumes in HTS-sucrose, and centrifuged at 1,000 xg for 10 minutes. The resultant pellet (P1) is discarded and supernatant centrifuged at 20,000 xg for 20 minutes. The resultant pellet (P2) is resuspended in HTS and centrifuged at 8,000 xg for 20 minutes. The supernatant and outer buffy coat (remaining pellet core discarded) is centrifuged at 20,000 xg for 20 minutes. The resultant pellet (P2/P3) is resuspended in HTS containing 1 mM EDTA and centrifuged at 20,000 xg for 20 minutes. The P2/P3 pellet is resuspended in HTS and the "washing" procedure is repeated two more times. The P2/P3 pellet is then resuspended in 5 volumes of HTS, frozen on dry-ice and stored at −80° C. for at least 72 hours prior to binding assay.

At the time of the assay, the appropriate amount of tissue is thawed and resuspended in 50 mM Hepes-KOH buffer (pH 8.0 at 4° C.) and "washed" twice by resuspension and centrifugation at 20,000 xg for 20 minutes. The binding of [$^3$H]5,7DCKA is performed as described by Baron et al. *Env. J. Pharmacol* 206: 149-154 (1991). Assays are performed at 4° C. using quadruplicate samples in a total volume/tube of 1-ml consisting of: 500 ul membrane suspension ( 200-300 ug protein/assay tube) in 50 mM Hepes-KOH buffer (pH 8.0 at 4° C.), 100 ul [$^3$H]5,7DCKA solution (19-21 nM; specific activity 18.2 Ci/mmol), 100 ul drug or buffer, and 300 ul buffer. Glycine or 7-chlorokynurenic acid (100 uM) is used to define nonspecific binding. Felbamate, solutions of 10 mM and 100 mM, are dissolved in 40-50% and 100% DMSO, respectively, and serial dilutions are performed. Binding reactions are initiated by adding the tissue homogenate and terminated after a 15 minute incubation period by rapid filtration through Brandel GF/B filters using a Brandel M-24 cell harvester. This filtration is followed by two 5-ml rinses with ice-cold buffer. Radioactivity is monitored in a Beckman LS 5801 liquid scintillation counter.

Inhibition of [$^3$H]5,7DCKA binding by glycine (10 nM-10 uM) or felbamate (10 uM-10 mM) is performed to assess the potencies of these compounds for strychnine-insensitive glycine receptors. Displacement curves and $IC_{50}$ values were analyzed using Graphpad (ISI Software, Philadelphia, Pa.). The $K_1$ values were calculated using the equation: $K_1 = IC_{50}/1 + [L]/K_D$, where [L] is the concentration of [$^3$H]5,7DCKA (19-21 nM) used in the assay and $K_D$ is the dissociation constant of [$^3$H]5,7DCKA (69 nM).

Displacement of [$^3$H]5,7DCKA by glycine (10 nM 10 uM) yielded an $IC_{50}$ of 371 nM (FIG. 1). Inhibition of [$^3$H]5,7DCKA by felbamate (10 uM-10 mM) resulted in an $IC_{50}$ value of 374 uM (FIG. 2). The $IC_{50}$ shown in FIG. 2 is generated by combining and then plotting on a single graph the felbamate displacement data from three separate experiments. A Hill slope (−0.93) of these data demonstrated unity and indicated interaction with a single population of sites. The $IC_{50}$ value (mean +/− SEM) from the felbamate displacement experiments presented is calculated to be 477 +/− 49 uM. The K estimates for inhibition of [$^3$H]5,7DCKA were: glycine, 284 nM (FIG. 1); felbamate, 289 uM; and felbamate (mean +/− SEM), 368 +/− 37 uM (FIG. 2).

The $IC_{50}$ value obtained from glycine inhibition of [$^3$H]5,7DCKA (FIG. 1) corresponds well with previously reported data. Moreover, results obtained demonstrate that felbamate interacts with strychnine-insensitive glycine receptors at relatively high concentrations. These conclusions are based on displacement data illustrating that felbamate competitively inhibits [$^3$H]5,7DCKA) binding to rat forebrain membranes (FIG. 2).

EXAMPLE II

Sprague-Dawley rats are briefly anesthetized with Halothane and then decapitated. The brain is removed and the hippocampus dissected. Transverse hippocampal brain slices of 475 microns are sectioned with a McIlwain tissue chopper. Slices are then incubated in a temperature controlled chamber of 34 degrees centigrade while being perfused with an artificial cerebral spinal fluid (NaCl 126 mM; KCl, 4; $KH_2PO_4$, 1.4; $MgSO_4$, 1.3; $CaCl_2$, 2.4; $NaHCO_3$, 26 and glucose, 4) saturated with 95% $O_2$ and 5% $CO_2$.

After an initial one hour equilibration period, the slices are tested for electrophysiological function. Electrical stimulation is given in the region of the CA3 collaterals with a bipolar twisted wire electrode. Evoked responses are recorded extracellularly in the pyramidal cell layer of the CA1 region. Stimulation is given for a duration of 40 microseconds in square wave pulses. The peak-to-peak amplitude of the resultant evoked potential response is then monitored.

Hippocampal slices from one animal are placed in two chambers. One chamber is used as a control and receives standard artificial cerebral spinal fluid (ACSF) while the second receives felbamate. In each chamber, one slice is stimulated every 30 seconds to monitor evoked potential response. Other slices in the chamber are not continuously stimulated. In these latter slices, designated as non-stimulated, the evoked potential response is assessed only at the beginning and end of the experiment. Only slices with initial evoked potentials of 3 mV or greater amplitude are included for testing.

The experimental chamber is perfused with oxygenated artificial cerebral spinal fluid (ACSF) containing felbamate for 30 minutes before the initiation of hypoxic conditions. The control chamber continues to receive oxygenated ACSF without felbamate during this period. Hypoxic conditions are then initiated simultaneously in both chambers by changing to perfusing media saturated with 95% $N_2$ and 5% $CO_2$. The experimental chamber receives nitrogenated ACSF with felbamate while the control chamber receives nitrogenated ACSF without felbamate.

The duration of hypoxic exposure for both chambers is determined by the disappearance of the hypoxic injury potential (HIP) in the control stimulated slice. This potential appears during hypoxia after the disappearance of the original evoked potential. Although hippocampal slices can vary in their temporal response to hypoxia, the HIP is a reliable marker of permanent hypoxic injury. For this reason, the disappearance of the HIP is chosen to determine length of hypoxic exposure. Hypoxia is continued in both chambers for 5 minutes beyond the disappearance of the HIP in the stimulated control slice.

After hypoxic exposure, slices are monitored through one hour of recovery with oxygenated ACSF. The felbamate chamber receives oxygenated ACSF with felbamate for the first 15 minutes of this recovery and then standard oxygenated ACSF for the remaining 45 minutes of recovery. After a one-hour recovery period, the percentage of evoked potential amplitude recovery is assessed in both stimulated and non-stimulated slices. This percentage is calculated as the evoked potential amplitude after recovery divided by the evoked potential amplitude prior to hypoxic exposure.

The results of the foregoing procedure are as follows:
a. Pre-hypoxic Incubation.

Felbamate perfusion produced occasional transient collapse and disappearance of the evoked potential, but no evidence of toxicity as evidenced by permanent potential loss was seen.

b Hypoxic Neuroprotection.

Significant neuroprotection against hypoxia is seen at felbamate concentrations of 380 uM, 840 uM, 1,300 uM and 1,700 uM.

This protective action is assessed by several measures. First, evoked potential recovery is assessed in both stimulated and non-stimulated slices. Additionally, hypoxic protection is calculated for both stimulated and non-stimulated slices. This measure is calculated as the damage seen in control slices minus the damage seen in experimental (felbamate) slices divided by the damage seen in control slices. For these purposes damage is defined as 100 percent minus percent recovery. The determination of hypoxic protection helps take into account any survival seen in control slices. Lastly, counts of total surviving slices were made. For this purpose a minimal amplitude criteria of 3 mV was used as the indicator of a surviving slice.

In stimulated control slices, hypoxic exposure resulted in near complete loss (1.0% mean recovery) of the population spike, while slices treated with 4, 190, 380, 840, 1,300 and 1,700 uM felbamate showed respectively 2%, 6%, 13%, 46%, 95% and 96% recovery. This recovery is significant at p 0.05 for 840 uM and significant at p 0.001 for concentrations of 1,300 and 1,700 uM. Since recovery in the stimulated control slices is minimal, calculated protection was essentially identical to recovery. Counts of surviving stimulated slices indicated substantial felbamate protection at doses of 1,300 and 1,700 uM. Interestingly, 1,700 uM felbamate delayed the appearance of the HIP by 14.5 minutes (p 0.05) but did not affect the disappearance of the evoked potential.

In non-stimulated control slices, recovery from hypoxic exposure shows greater recovery than stimulated control slices and a mean non-stimulated control recovery of 30% is seen. Calculated protection with felbamate concentrations of 4, 190, 380, 840, 1,300 and 1,700 uM, show respective values of 4%, 63%, 48%, 100% and 100%. Additionally, counts of surviving non-stimulated slices showed substantial protection.

The foregoing example indicates a significant hypoxic neuroprotective effect with felbamate within a wide concentration range (380 to 1,700 uM) in the hippocampal slice hypoxic model. Felbamate's hypoxic $EC_{50}$ in vitro appears to fall between its anticonvulsant $ED_{50}$ for MES (46 mg/kg) and metrazol (238 mg/kg) in rats. At high concentration of felbamate, no evidence of toxicity for electrophysiological function is seen.

As previously stated, glycine augments NMDA receptor-mediated membrane depolarization and is required for activation of NMDA-gated calcium channels. Furthermore, excessive activation of this "supramolecular complex" (e.g., by excitatory amino acids) has been shown to be associated with seizure disorders, ischemic brain damage and other neuropathologies. Compounds such as felbamate that interact with the strychnine-insensitive glycine modulatory site appear to alter the effects of glycine on the NMDA-gated channels. Thus, the data presented here support a mechanism for felbamate's neuroprotective effects via glycine receptor interaction.

The compounds of this invention can be administered for the treatment of central nervous system disorders associated with or resulting from excessive activation of NMDA receptor complex according to the invention by any means that effects contact of the active ingredient compound with the site of action in the body of a warm-blooded animal. For example, administration can be parenteral, i.e. subcutaneous, intravenous, intramuscular or intraperitoneal. Alternatively, or concurrently, in most cases administration will be by the oral route.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from about 100 to about 500 milligrams per day in one or more applications is effective to obtain desired results.

The active ingredient can be administered orally in solid dosage forms, such as capsules, tablets and powders, or in liquid dosage forms such as elixirs syrups and suspensions. It can also be administered parenterally in sterile liquid dosage forms.

Gelatin capsules contain the active ingredient and powdered carriers such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase patient acceptance.

In general, water, a suitable oil, saline, aqueous dextrose (glucose) and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite or ascorbic acid, either alone or combined, are suitable stabilizing agents. Also used are citric acid and its salts and sodium EDTA. In addition, parenteral solutions can contain preservatives such as benzalkonium chloride, methyl- or propylparaben and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When the drugs are administered in physical combination, the dosage form and administration route should be selected for compatibility with both drugs.

The percentage of 2-phenyl-1,3-propanediol dicarbamate in the compositions may be varied over wide limits and the quantity of medicament furnished by each individual tablet or capsule is relatively unimportant since the indicated total daily dose can be reached by administering either one or a plurality of capsules or tablets.

In general, an effective daily dose of the active ingredient is in the range of from about 100 milligrams to about 5 grams.

Felbamate (2-phenyl-1,3-propanediol dicarbamate) has a very favorable preclinical profile characterized by a substantial margin of safety (protective index 16.9–19.1).

It should be understood that the above examples are illustrative of the best mode only of the invention herein disclosed. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

What is claimed is:

1. A method for treating and controlling the symptoms of neuropsychopharmacological disorders associated with or resulting from excessive activation of the N-methyl-D-aspartate receptor complex which comprises administering to a human or other warm-blooded animal from about 1 to about 500 milligrams of the compound 2-phenyl-1,3-propanediol dicarbamate which possesses agonist properties for the strychnine-insensitive glycine modulatory site of the N-methyl-D-aspartate receptor complex.

2. A method for the treatment and control of the symptoms of neurodegenerative disorders associated with excessive activation of the N-methyl-D-aspartate receptor complex in a human or other warm-blooded animal patient in need of such treatment which comprises administering to said patient from about 1 to about 500 milligrams of 2-phenyl-1,3-propanediol dicarbamate.

3. A method as claimed in claim 2 wherein said neurodegenerative disorder is Alzheimer's disease.

4. A method as claimed in claim 2 wherein said neurodegenerative disorder is Parkinson's disease.

* * * * *